(12) United States Patent
Linker et al.

(10) Patent No.: US 6,608,004 B2
(45) Date of Patent: Aug. 19, 2003

(54) SUBSTITUTED 2-ARYL-1,2,4-TRIAZINE-3,5-DI(THI)ONES

(75) Inventors: Karl-Heinz Linker, Leverkusen (DE); Joachim Kluth, Langenfeld (DE); Mark Wilhelm Drewes, Langenfeld (DE); Peter Dahmen, Neuss (DE); Dieter Feucht, Monheim (DE); Rolf Pontzen, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/980,274

(22) PCT Filed: May 24, 2001

(86) PCT No.: PCT/EP00/04704

§ 371 (c)(1),
(2), (4) Date: Nov. 29, 2001

(87) PCT Pub. No.: WO00/75119

PCT Pub. Date: Dec. 14, 2000

(65) Prior Publication Data

US 2003/0069140 A1 Apr. 10, 2003

(30) Foreign Application Priority Data

Jun. 4, 1999 (DE) .......................... 199 25 593

(51) Int. Cl.⁷ .................. C07D 253/075; A01N 43/707
(52) U.S. Cl. ..................... 504/229; 504/225; 544/112; 544/182
(58) Field of Search ................ 544/182, 112; 504/229, 225

(56) References Cited

U.S. PATENT DOCUMENTS

| | | | |
|---|---|---|---|
| 4,755,217 A | 7/1988 | Chang et al. | 71/93 |
| 4,878,941 A | 11/1989 | Theodoridis | 71/93 |
| 4,906,286 A | 3/1990 | Lyga | 71/93 |
| 4,956,004 A | 9/1990 | Theodoridis | 71/93 |
| 5,262,390 A | 11/1993 | Theodoridis | 504/273 |
| 5,344,812 A | 9/1994 | Theodoridis | 504/243 |

FOREIGN PATENT DOCUMENTS

| | | |
|---|---|---|
| EP | 0 011 693 | 6/1980 |
| WO | 97/30980 | 8/1997 |

*Primary Examiner*—John M. Ford
(74) *Attorney, Agent, or Firm*—Richard E. L. Henderson

(57) ABSTRACT

The invention relates to novel substituted 2-aryl-1,2,4-triazine-3,5-di(thi)ones of the general formula (I),

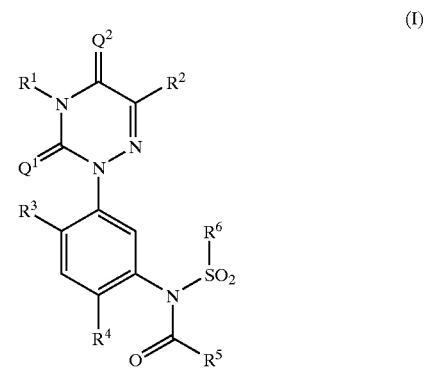

in which $Q^1$, $Q^2$, $R^1$, $R^2$, $R^3$, $R^4$, $R^5$ and $R^6$ are each as defined in the description, and to processes for their preparation and to their use as herbicides.

30 Claims, No Drawings

SUBSTITUTED 2-ARYL-1,2,4-TRIAZINE-3,5-DI(THI)ONES

This is a 371 of PCT/EP00/04704, filed May 24, 2001.

The invention relates to novel substituted 2-aryl-1,2,4-triazine-3,5-di(thi)ones, to processes for their preparation and to their use as herbicides.

It is known that certain substituted 2-aryl-1,2,4-triazin-(ethi)ones have herbicidal properties (cf. EP-A-11693, EP-A-271170, WO-A-86/00072, WO-A-97/30980, U.S. Pat. Nos. 4,755,217, 4,878,941, 4,956,004, 5,262,390, 5,344,812). However, the compounds known from the patent applications or patents stated have not attained any importance worth mentioning.

This invention, accordingly, provides novel substituted 2-aryl-1,2,4-triazine-3,5-di(thi)ones of the general formula (I)

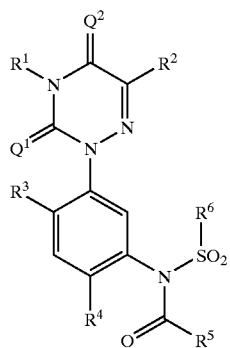

in which $Q^1$ represents oxygen or sulphur, $Q^2$ represents oxygen or sulphur, $R^1$ represents hydrogen, cyano, amino, represents in each case optionally cyano-, halogen- or $C_1$–$C_4$-alkoxy-substituted alkyl, alkoxy, alkylamino, dialkylamino, alkylcarbonyl or alkoxycarbonyl having in each case 1 to 6 carbon atoms in the alkyl groups, represents in each case optionally halogen-substituted alkenyl, alkenylcarbonyl, alkenyloxycarbonyl, alkinyl, alkinylcarbonyl or alkinyloxycarbonyl having in each case 2 to 6 carbon atoms in the alkenyl or alkinyl groups, or represents in each case optionally cyano-, halogen- or $C_1$–$C_4$-alkyl-substituted cycloalkyl or cycloalkylalkyl having in each case 3 to 6 carbon atoms in the cycloalkyl groups and optionally 1 to 4 carbon atoms in the alkyl moiety, $R^2$ represents hydrogen, halogen, nitro, carboxyl, cyano, thiocarbamoyl, amino, represents in each case optionally cyano-, halogen- or $C_1$–$C_4$-alkoxy-substituted alkyl, alkoxy, alkylthio, alkylamino or dialkylamino having in each case 1 to 6 carbon atoms in the alkyl groups, represents in each case optionally halogen-substituted alkenyl, alkenyloxy, alkenylthio, alkinyl, alkinyloxy or alkinylthio having in each case 2 to 6 carbon atoms in the alkenyl or alkinyl groups, or represents in each case optionally cyano-, halogen- or $C_1$–$C_4$-alkyl-substituted cycloalkyl or cycloalkylalkyl having in each case 3 to 6 carbon atoms in the cycloalkyl groups and optionally 1 to 6 carbon atoms in the alkyl moiety, $R^3$ represents hydrogen, cyano or halogen, $R^4$ represents cyano or thiocarbamoyl, $R^5$ represents hydrogen, represents alkoxycarbonyl having 1 to 6 carbon atoms in the alkoxy group, or represents one of the radicals —$R^7$, —O—$R^7$, —$SR^7$, —NH—$R^7$ or —$NR^7R^8$, $R^6$ represents amino, hydroxyl or represents one of the radicals —$R^7$ or —$NR^7R^8$, $R^7$ represents straight-chain or branched alkyl having 1 to 10 carbon atoms which is optionally mono- or polysubstituted by identical or different substituents, possible substituents being:

cyano, carboxyl, carbamoyl, thiocarbamoyl, halogen, in each case straight-chain or branched alkoxy, alkoxyalkoxy, alkylcarbonyloxy, alkylthio, alkylsulphinyl, alkylsulphonyl, alkoxycarbonyl, N-alkyl-aminocarbonyl, N,N-dialkyl-aminocarbonyl, trialkylsilyl or alkylsulphonylaminocarbonyl having in each case 1 to 6 carbon atoms in the individual alkyl moieties, or heterocyclyl, where the heterocyclyl radical is a five- to seven-membered, optionally benzo-fused, saturated or unsaturated heterocycle having 1 to 3 identical or different heteroatoms, in particular nitrogen, oxygen and/or sulphur, or $R^7$ represents alkenyl or alkinyl having in each case 2 to 8 carbon atoms and being in each case optionally mono- or polysubstituted by identical or different halogens, or $R^7$ represents cycloalkyl or cycloalkylalkyl having in each case 3 to 7 carbon atoms in the cycloalkyl groups and optionally 1 to 4 carbon atoms in the alkyl moiety and being in each case optionally mono- or polysubstituted by identical or different substituents from the group consisting of cyano, halogen and $C_1$–$C_4$-alkyl, or $R^7$ represents aryl, arylalkyl, bis-aryl-alkyl, arylalkenyl, aryloxyalkyl or arylalkoxyalkyl having in each case 6 to 10 carbon atoms in the aryl moiety and optionally up to 4 carbon atoms in the straight-chain or branched alkyl moiety or alkenyl moiety and being in each case optionally mono- or polysubstituted in the aryl moiety by identical or different substituents, or represents a saturated or unsaturated five- to seven-membered heterocyclyl radical having 1 to 3 identical or different heteroatoms—in particular nitrogen, oxygen and/or sulphur—and being optionally mono- or polysubstituted by identical or different substituents and/or benzo-fused, possible aryl or heterocyclyl substituents being:

halogen, cyano, nitro, amino, methylenedioxy, N-($C_1$–$C_4$-alkyl-carbonyl)-amino, in each case straight-chain or branched alkyl, alkoxy, alkylthio, alkylsulphinyl or alkylsulphonyl having in each case 1 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 3 identical or different halogen atoms, in each case straight-chain or branched alkoxycarbonyl or alkoximinoalkyl having in each case 1 to 6 carbon atoms in the individual alkyl moieties and phenyl which is optionally mono- or polysubstituted by identical or different substituents from the group consisting of halogen and straight-chain or branched alkyl or alkoxy having in each case 1 to 6 carbon atoms and straight-chain or branched halogenoalkyl or halogenoalkoxy having in each case 1 to 6 carbon atoms and 1 to 3 identical or different halogen atoms, and $R^8$ represents hydrogen or represents straight-chain or branched alkyl having 1 to 8 carbon atoms which is optionally mono- or polysubstituted by identical or different substituents, possible substituents being:

cyano, carboxyl, carbamoyl, thiocarbamoyl, halogen, in each case straight-chain or branched alkoxy, alkoxyalkoxy, alkylthio, alkylsulphinyl, alkylsulphonyl, alkoxycarbonyl, alkylaminocarbonyl, dialkylaminocarbonyl, trialkylsilyl or alkylsulphonylaminocarbonyl having in each case 1 to 8 carbon atoms in the individual alkyl moieties or heterocyclyl, where the heterocyclyl radical is a five- to seven-membered, optionally benzo-fused, saturated or unsaturated heterocycle having 1 to 3 identical or different heteroatoms, in particular nitrogen, oxygen and/or sulphur, or $R^8$ represents alkenyl or alkinyl having in each case 2 to 8 carbon atoms and being in each case optionally mono- or polysubstituted by identical or different halogens, or $R^8$ represents cycloalkyl having 3 to 7 carbon atoms which is optionally mono- or polysubstituted by identical or different substituents from the group consisting of cyano, halogen and straight-chain or branched alkyl having 1 to 4 carbon atoms, or $R^8$ together with $R^7$ represents alkanediyl (alkylene) having 2 to 6 carbon atoms which is optionally interrupted by O (oxygen), S (sulphur), NH or N—($C_1$–$C_4$-alkyl).

Preferred substituents or ranges of the radicals present in the formulae shown above and below are defined below.

$R^1$ preferably represents hydrogen, cyano, amino, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i-, s- or t-butylamino, dimethylamino, diethylamino, acetyl, propionyl, n- or i-butyroyl, methoxycarbonyl, ethoxycarbonyl, n- or i-propoxycarbonyl, represents in each case optionally fluorine-, chlorine- or bromine-substituted propenyl, butenyl, propenylcarbonyl, butenylcarbonyl, propenyloxycarbonyl, butenyloxycarbonyl, represents propinyl, butinyl, propinylcarbonyl, butinylcarbonyl, propinyloxycarbonyl or butinyloxycarbonyl, or represents in each case optionally cyano-, fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl.

$R^2$ preferably represents hydrogen, nitro, carboxyl, cyano, thiocarbamoyl, amino, fluorine, chlorine, bromine, represents in each case optionally cyano-, fluorine-, chlorine-, methoxy- or ethoxy-substituted methyl, ethyl, n- or i-propyl, n-, i- s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, represents in each case optionally fluorine-, chlorine- or bromine-substituted propenyl, propenyloxy, propenylthio, butenyl, butenyloxy or butenylthio, represents propinyl, propinyloxy, propinylthio, butinyl, butinyloxy or butinylthio, or represents in each case optionally cyano-, fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl.

$R^3$ preferably represents hydrogen, fluorine or chlorine.

$R^5$ preferably represents hydrogen, methoxycarbonyl, ethoxycarbonyl, n- or i-propoxycarbonyl, or represents one of the radicals —$R^7$, —O—$R^7$, —S—$R^7$, —NH—$R^7$ or —$NR^7R^8$.

$R^7$ preferably represents methyl, ethyl, n- or i-propyl, n-, i-, s- or t-butyl, n-, i-, s-, t- or neo-pentyl, n-, i- or s-hexyl, each of which is optionally mono- or disubstituted, preferred possible substituents being in each case:

cyano, carboxyl, carbamoyl, fluorine, chlorine, bromine, methoxy, ethoxy, n- or i-propoxy, methoxymethoxy, ethoxymethoxy, methoxyethoxy, ethoxyethoxy, acetylmethoxy, methylthio, ethylthio, n- or i-propylthio, methylsulphinyl, ethylsulphinyl, methylsulphonyl, ethylsulphonyl, methoxycarbonyl, ethoxycarbonyl, methylaminocarbonyl, ethylaminocarbonyl, dimethylaminocarbonyl, trimethylsilyl, methylsulphonylaminocarbonyl or ethylsulphonylaminocarbonyl.

$R^7$ furthermore preferably represents ethenyl, propenyl, butenyl, ethinyl, propinyl or butinyl, each of which is optionally mono- or disubstituted by fluorine and/or chlorine.

$R^7$ furthermore preferably represents cyclopropyl, cyclobutyl, cyclopentyl, cyclohexyl, cyclopropylmethyl, cyclopropylethyl, cyclopentylmethyl, cyclopentylethyl, cyclohexylmethyl or cyclohexylethyl, each of which is optionally mono- or disubstituted by identical or different substituents from the group consisting of fluorine, chlorine, methyl and ethyl.

$R^7$ furthermore preferably represents phenyl, benzyl, phenylethyl, phenylpropyl, 2,2-bis-phenyl-ethyl, phenylethenyl, phenoxymethyl, phenoxyethyl, phenoxypropyl, furyl, furylmethyl, thienyl, oxazolyl, isoxazolyl, thiazolyl, pyrazolyl, oxadiazolyl, thiadiazolyl, pyridinyl, pyridinylmethyl, pyrimidinyl, pyrrolidinyl, piperidinyl, morpholinyl or chromanyl, each of which is optionally mono-, di- or trisubstituted by identical or different substituents, preferred possible substituents being in each case:

fluorine, chlorine, bromine, cyano, nitro, amino, methylenedioxy, N-acetylamino, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, methylsulphonyl, trifluoromethyl, difluoromethyl, trifluoromethoxy, difluoromethoxy, trifluoromethylthio, trifluoromethylsulphinyl, trifluoromethylsulphonyl, methoxycarbonyl, ethoxycarbonyl, methoximinomethyl, methoximinoethyl, ethoximinomethyl, ethoximinoethyl.

$R^8$ preferably represents hydrogen or represents in each case optionally monosubstituted methyl, ethyl, n- or i-propyl, n- or i-butyl, preferred possible substituents being:

cyano, carboxyl, carbamoyl, fluorine, chlorine, methoxy, ethoxy, n- or i-propoxy, methoxymethoxy, ethoxymethoxy, methoxyethoxy, ethoxyethoxy, methylthio, ethylthio, n- or i-propylthio, methylsulphinyl, ethylsulphinyl, methylsulphonyl, ethylsulphonyl, methoxycarbonyl, ethoxycarbonyl, methylaminocarbonyl, ethylaminocarbonyl, dimethylaminocarbonyl.

$R^8$ furthermore preferably represents ethenyl, propenyl, butenyl, ethinyl, propinyl or butinyl, each of which is optionally mono- or disubstituted by fluorine and/or chlorine.

$R^8$ furthermore preferably represents cyclopropyl, cyclopentyl or cyclohexyl, each of which is optionally mono- or disubstituted by identical or different substituents from the group consisting of fluorine, chlorine, methyl and ethyl.

$R^8$ together with $R^7$ furthermore preferably represents butane-1,4-diyl, pentane-1,5-diyl or 3-oxa-pentane-1,5-diyl.

$R^1$ particularly preferably represents hydrogen or represents in each case optionally fluorine-substituted methyl, ethyl, n- or i-propyl.

$R^2$ particularly preferably represents hydrogen, cyano, fluorine, chlorine, bromine or represents in each case optionally fluorine-substituted methyl, ethyl, n- or i-propyl.

$R^5$ particularly preferably represents hydrogen or represents one of the radicals —$R^7$, —O—$R^7$, —S—$R^7$, —NH—$R^7$ or —N$R^7R^8$.

$R^7$ particularly preferably represents in each case optionally mono- or disubstituted methyl, ethyl, n- or i-propyl, n-, i-, s- or t-butyl, n-, i-, s-, t- or neo-pentyl, preferred possible substituents being in each case:
  cyano, fluorine, chlorine, bromine, methoxy, ethoxy, n- or i-propoxy, methoxymethoxy, ethoxymethoxy, methoxyethoxy, ethoxyethoxy, acetyloxymethyl, acetylmethoxy.

$R^7$ furthermore particularly preferably represents ethenyl, propenyl, butenyl, ethinyl, propinyl or butinyl, each of which is optionally mono- or disubstituted by fluorine and/or chlorine.

$R^7$ furthermore particularly preferably represents cyclopropyl, cyclobutyl, cyclopentyl, cyclohexyl, cyclopropylmethyl, cyclopropylethyl, cyclopentylmethyl, cyclopentylethyl, cyclohexylmethyl or cyclohexylethyl, each of which is optionally mono- or disubstituted by identical or different substituents from the group consisting of fluorine, chlorine, methyl and ethyl.

$R^7$ furthermore particularly preferably represents phenyl, benzyl, phenylethyl, phenylpropyl, 2,2-bis-phenylethyl, phenylethenyl, phenoxymethyl, phenoxyethyl, phenoxypropyl, furyl, thienyl, oxazolyl, isoxazolyl, thiazolyl, pyrazolyl, oxadiazolyl, thiadiazolyl, pyridinyl, pyrimidinyl, pyrrolidinyl, piperidinyl or chromanyl, each of which is optionally mono-, di- or trisubstituted by identical or different substituents, preferred possible substituents being in each case:
  fluorine, chlorine, bromine, cyano, nitro, methylenedioxy, methyl, ethyl, n- or i-propyl, n-, i-, s- or t-butyl, methoxy, ethoxy, n- or i-propoxy, methylthio, ethylthio, methylsulphinyl, methylsulphonyl, trifluoromethyl, difluoromethyl, trifluoromethoxy, difluoromethoxy.

$R^8$ particularly preferably represents hydrogen or represents in each case optionally monosubstituted methyl, ethyl, n- or i-propyl, n- or i-butyl, preferred possible substituents being:
  cyano, fluorine, chlorine, methoxy, ethoxy, n- or i-propoxy.

$R^8$ furthermore particularly preferably represents ethenyl, propenyl, butenyl, ethinyl, propinyl or butinyl, each of which is optionally mono- or disubstituted by fluorine and/or chlorine.

$R^8$ furthermore particularly preferably represents cyclopropyl, cyclopentyl or cyclohexyl, each of which is optionally mono- or disubstituted by identical or different substituents from the group consisting of fluorine, chlorine, methyl and ethyl.

$R^1$ most preferably represents methyl, ethyl or n- or i-propyl.

$R^2$ most preferably represents hydrogen.

$R^3$ most preferably represents fluorine or chlorine.

$R^6$ most preferably represents methyl, ethyl or n- or i-propyl.

The abovementioned general or preferred radical definitions apply both to the end products of the formula (I) and, correspondingly, to the starting materials or intermediates required in each case for the preparation. These radical definitions can be combined with one another as desired, i.e. including combinations between the given preferred ranges.

Preference according to the invention is given to those compounds of the formula (I) which contain a combination of the meanings given above as being preferred.

Particular preference according to the invention is given to those compounds of the formula (I) which contain a combination of the meanings given above as being particularly preferred.

Most preference according to the invention is given to those compounds of the formula (I) which contain a combination of the meanings given above as being most preferred.

Saturated or unsaturated hydrocarbon radicals, such as alkyl or alkenyl, are—including in combination with heteroatoms, such as in alkoxy—in each case straight-chain or branched as far as this is possible.

Optionally substituted radicals can be mono- or polysubstituted, where in the case of polysubstitution the substituents can be identical or different.

The novel substituted 2-aryl-1,2,4-triazine-3,5-di(thi)ones of the general formula (I) have interesting biological properties. In particular, they have strong herbicidal activity.

The novel substituted 2-aryl-1,2,4-triazine-3,5-di(thi)ones of the general formula (I) are obtained when 2-aryl-1,2,4-triazine-3,5-di(thi)ones of the general formula (II)

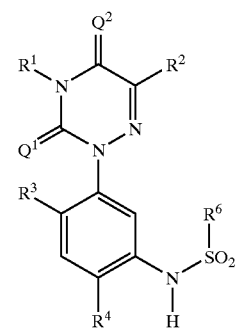

(II)

in which $Q^1$, $Q^2$, $R^1$, $R^2$, $R^3$, $R^4$ and $R^6$ are each as defined above, are reacted with halogenocarbonyl compounds of the general formula (III)

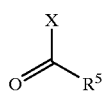

(III)

in which
R⁵ is as defined above and
X represents halogen,
if appropriate in the presence of a reaction auxiliary and if appropriate in the presence of a diluent.

Using, for example, 2-(4-cyano-2-fluoro-5-methylsulphonylamino-phenyl)-4-methyl-1,2,4-triazine-3,5 (2H,4H)-dione and propionic acid chloride as starting materials, the course of the reaction in the process according to the invention can be illustrated by the following formula scheme:

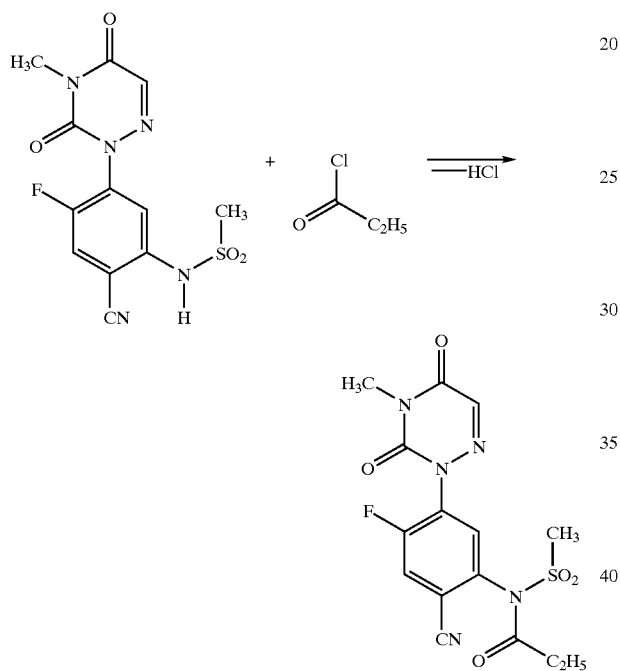

The formula (II) provides a general definition of the 2-aryl-1,2,4-triazine-3,5-di(thi)ones to be used as starting materials in the process according to the invention for preparing compounds of the general formula (I). In the general formula (II), $Q^1$, $Q^2$, $R^1$, $R^2$, $R^3$, $R^4$ and $R^6$ each preferably or in particular have those meanings which have already been mentioned above, in connection with the description of the compounds of the general formula (I) according to the invention, as being preferred or as being particularly preferred for $Q^1$, $Q^2$, $R^1$, $R^2$, $R^3$, $R^4$ and $R^6$.

The starting materials of the general formula (II) are known and/or can be prepared by processes known per se (cf. WO-A-97/30980, Preparation Examples).

The formula (III) provides a general definition of the halogenocarbonyl compounds further to be used as starting materials in the process according to the invention for preparing compounds of the general formula (I). In the general formula (III), $R^5$ preferably or in particular has that meaning which has already been mentioned above, in connection with the description of the compounds of the general formula (I) according to the invention, as being preferred or as being particularly preferred for $R^5$; X preferably represents fluorine, chlorine or bromine, in particular chlorine.

The starting materials of the general formula (III) are known organic chemicals for synthesis.

Suitable reaction auxiliaries for the process according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

Further suitable reaction auxiliaries for the process according to the invention are also phase-transfer catalysts. Examples of such catalysts which may be mentioned are:

Tetrabutylammonium bromide, tetrabutylammonium chloride, tetraoctylammonium chloride, tetrabutylammonium hydrogen sulphate, methyl-trioctylammonium chloride, hexadecyl-trimethylammonium chloride, hexadecyl-trimethylammonium bromide, benzyl-trimethylammonium chloride, benzyl-triethylammonium chloride, benzyl-trimethylammonium hydroxide, benzyl-triethylammonium hydroxide, benzyl-tributylammonium chloride, benzyl-tributylammonium bromide, tetrabutylphosphonium bromide, tetrabutylphosphonium chloride, tributyl-hexadecylphosphonium bromide, butyl-triphenylphosphonium chloride, ethyl-trioctylphosphonium bromide, tetraphenylphosphonium bromide.

Suitable diluents for carrying out the process according to the invention are, in addition to water, especially inert organic solvents. These include, in particular, aliphatic, alicyclic or aromatic, optionally halogenated hydrocarbons, such as, for example benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

When carrying out the process according to the invention, the reaction temperatures can be varied within a relatively wide range. In general, the process is carried out at temperatures between 0° C. and 150° C., preferably between 10° C. and 120° C.

The process according to the invention is generally carried out under atmospheric pressure. However, it is also possible to carry out the process according to the invention under elevated or reduced pressure—in general between 0.1 bar and 10 bar.

For carrying out the process according to the invention, the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for several hours. Work-up is carried out by customary methods (cf. the Preparation Examples).

The active compounds according to the invention can be used as defoliants, desiccants, haulm killers and, especially, as weed killers. By weeds in the broadest sense there are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Sphenoclea, Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.

Monocotyledonous weeds of the genera: Echinochloa, Eriochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Dactyloctenium, Agrostis, Alopecurus, Apera, Aegilops, Phalaris.

Monocotyledonous crops of the genera: Oryza, Zea, Triticum, Hordeum, Avena, Secale, Sorghum, Panicum, Saccharum, Ananas, Asparagus, Allium.

However, the use of the active compounds according to the invention is in no way restricted to these genera, but also extends in the same manner to other plants.

According to the invention, it is possible to treat all plants and parts of plants. By plants are to be understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders certificates. Parts of plants are to be understood as meaning all above-ground and below-ground parts and organs of plants, such as shoot, leaf, flower and root, examples which may be mentioned being leaves, needles, stems, trunks, flowers, shoot-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

Depending on the concentration, the active compounds according to the invention are suitable for total weed control, for example on industrial terrain and rail tracks and on paths and areas with or without tree growth. Equally, the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention have strong herbicidal activity and a broad activity spectrum when used on the soil and on above-ground parts of plants. To a certain extent, they are also suitable for selective control of monocotyledonous and dicotyledonous weeds in monocotyledonous and dicotyledonous crops, both by the pre-emergence and by the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzobicyclon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlomitrofen, chlorsulfuron, chlorotoluron, cinidon(-ethyl), cinmethylin, cinosulfuron, clefoxydim, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop (-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron (-methyl), ethofumesate, ethoxyfen, ethoxysulfuron, etobenzanid, fenoxaprop(-P-ethyl), fentrazamide, flamprop (-isopropyl), flamprop(-isopropyl-L), flamprop(-methyl), flazasulfuron, florasulam, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate(-isopropylammonium), halosafen, haloxyfop(-ethoxyethyl), haloxyfop(-P-methyl), hexazinone, imazamethabenz(-methyl), imazamethapyr, imazamox, imazapic, imazapyr, imazaquin, imazethapyr, imazosulfuron, iodosulfuron(-methyl, -sodium), ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quinmerac, quinoclamine, quizalofop (-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the examples below.

PREPARATION EXAMPLES

Example 1

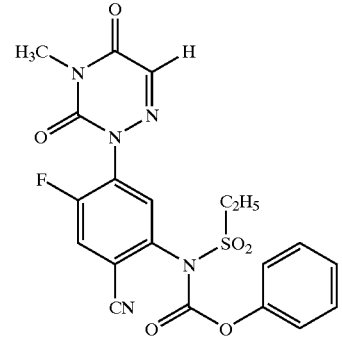

In 50 ml of acetonitrile, 1.8 g (5 mmol) of 2-(4-cyano-2-fluoro-5-ethylsulphonylamino-phenyl)-4-methyl-1,2,4-triazine-3,5(2H,4H)-dione and 1.01 g (10 mmol) of triethylamine are admixed with 1.57 g (10 mmol) of phenyl chloroformate, and the reaction mixture is stirred at 25° C. for 12 hours. The mixture is then concentrated using a rotary evaporator, the residue is stirred with water and acidified using conc. hydrochloric acid and precipitated solid is filtered off with suction and recrystallized from methanol.

This gives 1.9 g (80% of theory) of 2-[5-(N-phenoxy-carbonyl-N-ethylsulphonylamino)-4-cyano-2-fluoro-phenyl]-4-methyl-1,2,4-triazine-3,5(2H,4H)-dione of melting point 181° C.

log P (pH 2): 2.76

Example 2

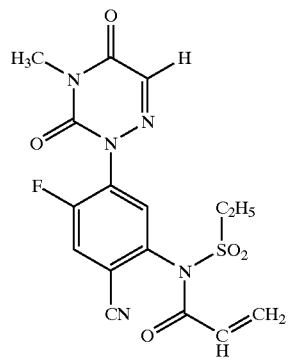

In 50 ml of acetonitrile, 1.4 g (4 mmol) of 2-(4-cyano-2-fluoro-5-ethylsulphonylamino-phenyl)-4-methyl-1,2,4-triazine-3,5(2H,4H)-dione and 0.8 g (8 mmol) of triethylamine are admixed with 1.0 g (0.8 mmol) of 3-chloropropionic acid chloride, and the reaction mixture is stirred at 25° C. for 12 hours. The mixture is then concentrated using a rotary evaporator, the residue is stirred with water and acidified using conc. hydrochloric acid, and the precipitated product is filtered off with suction and washed with water.

This gives 1.4 g (86% of theory) of 2-[5-(N-acryloyl-N-ethylsulphonylamino)-4-cyano-2-fluoro-phenyl]-4-methyl-1,2,4-triazine-3,5(2H,4H)-dione of melting point 118° C.

log P (pH 2): 1.97

Analogously to Examples 1 and 2, and in accordance with the general description of the preparation process according to the invention, it is also possible to prepare, for example, the compounds of the general formula (I) listed in Table 1 below.

TABLE 1

Examples of the compounds of the formula (I)
In all cases, $Q^1$ and $Q^2$ represent oxygen (I)

| Ex. No. | $R^1$ | $R^2$ | $R^3$ | $R^4$ | $R^5$ | $R^6$ | Physical Data |
|---|---|---|---|---|---|---|---|
| 3 | $CH_3$ | H | F | CN | phenyl | $C_2H_5$ | m.p.: 66° C. logP = 2.52[a] |
| 4 | $CH_3$ | H | F | CN | $CH_2Cl$ | $C_2H_5$ | m.p.: 100° C. logP = 2.09[a] |
| 5 | $CH_3$ | H | F | CN | 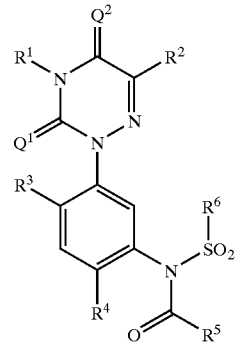 | $C_2H_5$ | m.p.: 176° C. logP = 2.52[a] |

TABLE 1-continued

Examples of the compounds of the formula (I)
In all cases, $Q^1$ and $Q^2$ represent oxygen (I)

| Ex. No. | $R^1$ | $R^2$ | $R^3$ | $R^4$ | $R^5$ | $R^6$ | Physical Data |
|---|---|---|---|---|---|---|---|
| 6 | $CH_3$ | H | F | CN | -CH$_2$-O-C$_6$H$_4$-Cl (4-Cl-phenoxymethyl) | $C_2H_5$ | m.p.: 65° C. logP = 3.07[a)] |
| 7 | $CH_3$ | H | F | CN | -CH(C$_2$H$_5$)(C$_4$H$_9$-n) | $C_2H_5$ | m.p.: 140° C. logP = 3.53[a)] |
| 8 | $CH_3$ | H | F | CN | 2-thienyl | $C_2H_5$ | m.p.: 102° C. logP = 2.54[a)] |
| 9 | $CH_3$ | H | F | CN | cyclopropyl | $C_2H_5$ | m.p.: 95° C. logP = 2.26[a)] |
| 10 | $CH_3$ | H | F | CN | $C(CH_3)_3$ | $C_2H_5$ | m.p.: 109° C. logP = 2.71[a)] |
| 11 | $CH_3$ | H | F | CN | 4-methoxyphenyl | $C_2H_5$ | m.p.: 94° C. logP = 2.77[a)] |
| 12 | $CH_3$ | H | F | CN | 4-chlorophenyl | $C_2H_5$ | m.p.: 82° C. logP = 3.13[a)] |
| 13 | $CH_3$ | H | F | CN | $CH(CH_3)_2$ | $C_2H_5$ | m.p.: 75° C. logP = 2.50[a)] |
| 14 | $CH_3$ | H | F | CN | 2-furyl | $C_2H_5$ | m.p.: 90° C. logP = 2.31[a)] |
| 15 | $CH_3$ | H | F | CN | -CH(OC$_2$H$_5$)(CH$_3$) | $C_2H_5$ | m.p.: 81° C. logP = 2.12[a)] |

TABLE 1-continued

Examples of the compounds of the formula (I)
In all cases, $Q^1$ and $Q^2$ represent oxygen

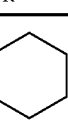

(I)

| Ex. No. | $R^1$ | $R^2$ | $R^3$ | $R^4$ | $R^5$ | $R^6$ | Physical Data |
|---|---|---|---|---|---|---|---|
| 16 | $CH_3$ | H | F | CN |  | $C_2H_5$ | m.p.: 182° C.<br>logP = 2.46[a) |
| 17 | $CH_3$ | H | F | CN | 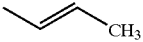 | $C_2H_5$ | m.p.: 80° C.<br>logP = 2.45[a) |
| 18 | $CH_3$ | H | F | CN |  $CH_3$ | $C_2H_5$ | m.p.: 153° C.<br>logP = 2.16[a) |
| 19 | $CH_3$ | H | F | CN | $CH_2C(CH_3)_3$ | $C_2H_5$ | m.p.: 155° C.<br>logP = 2.94[a) |
| 20 | $CH_3$ | H | F | CN | $CH_2CH(CH_3)_2$ | $C_2H_5$ | m.p.: 150° C.<br>logP = 2.65[a) |
| 21 | $CH_3$ | H | F | CN | 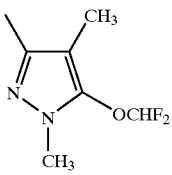 | $C_2H_5$ | m.p.: 122° C.<br>logP = 1.85[a) |
| 22 | $CH_3$ | H | F | CN | $(CH_2)_4Cl$ | $C_2H_5$ | m.p.: 60° C.<br>logP = 2.65[a) |
| 23 | $CH_3$ | H | F | CN | 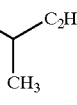 | $C_2H_5$ | m.p.: 187° C.<br>logP = 2.82[a) |
| 24 | $CH_3$ | H | F | CN | $\begin{matrix} C_2H_5 \\ | \\ CH \\ | \\ CH_3 \end{matrix}$ | $C_2H_5$ | m.p.: 134° C.<br>logP = 2.60[a) |
| 25 | $CH_3$ | H | F | CN | $CH_2OCH_3$ | $C_2H_5$ | m.p.: 154° C.<br>logP = 1.82[a) |
| 26 | $CH_3$ | H | F | CN | 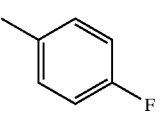 | $C_2H_5$ | m.p.: 123° C.<br>logP = 2.60[a) |
| 27 | $CH_3$ | H | F | CN | $(CH_2)_3Cl$ | $C_2H_5$ | m.p.: 132° C.<br>logP = 2.43[a) |
| 28 | $CH_3$ | H | F | CN | $CH_3$ | $C_2H_5$ | m.p.: 173° C.<br>logP = 1.79[a) |

TABLE 1-continued
Examples of the compounds of the formula (I)
In all cases, $Q^1$ and $Q^2$ represent oxygen
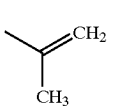
(I)
| Ex. No. | $R^1$ | $R^2$ | $R^3$ | $R^4$ | $R^5$ | $R^6$ | Physical Data |
|---|---|---|---|---|---|---|---|
| 29 | $CH_3$ | H | F | CN | 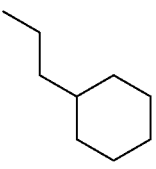 | $C_2H_5$ | m.p.: 146° C. logP = 2.26[a)] |
| 30 | $CH_3$ | H | F | CN | $(CH_2)_3Br$ | $C_2H_5$ | m.p.: 104° C. logP = 2.51[a)] |
| 31 | $CH_3$ | H | F | CN | 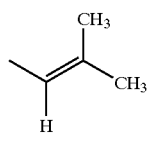 | $C_2H_5$ | m.p.: 123° C. logP = 3.66[a)] |
| 32 | $CH_3$ | H | F | CN | 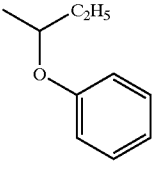 | $C_2H_5$ | m.p.: 150° C. logP = 2.40[a)] |
| 33 | $CH_3$ | H | F | CN | 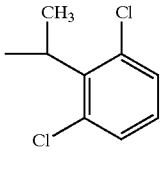 | $C_2H_5$ | m.p.: 128° C. logP = 3.12[a)] |
| 34 | $CH_3$ | H | F | CN | 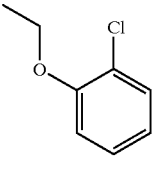 | $C_2H_5$ | m.p.: 159° C. logP = 3.07[a)] |
| 35 | $CH_3$ | H | F | CN |  | $C_2H_5$ | m.p.: 220° C. logP = 2.89[a)] |

TABLE 1-continued
Examples of the compounds of the formula (I)
In all cases, Q¹ and Q² represent oxygen
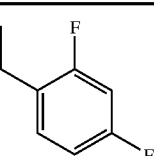
(I)
| Ex. No. | R¹ | R² | R³ | R⁴ | R⁵ | R⁶ | Physical Data |
|---|---|---|---|---|---|---|---|
| 36 | CH₃ | H | F | CN | 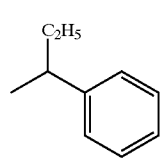 | C₂H₅ | m.p.: 210° C. logP = 2.73[a] |
| 37 | CH₃ | H | F | CN | 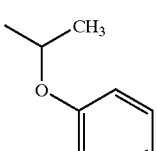 | C₂H₅ | m.p.: 190° C. logP = 3.12[a] |
| 38 | CH₃ | H | F | CN | 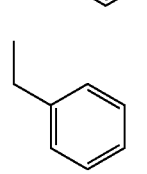 | C₂H₅ | m.p.: 115° C. logP = 2.93[a] |
| 39 | CH₃ | H | F | CN | 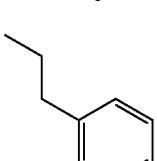 | C₂H₅ | m.p.: 132° C. logP = 2.85[a] |
| 40 | CH₃ | H | F | CN | 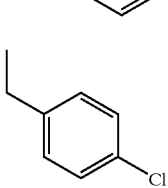 | C₂H₅ | m.p.: 194° C. logP = 2.61[a] |
| 41 | CH₃ | H | F | CN |  | C₂H₅ | m.p.: 136° C. logP = 2.88[a] |
| 42 | CH₃ | H | F | CN |  | C₂H₅ | m.p.: 222° C. logP = 2.96[a] |

TABLE 1-continued
Examples of the compounds of the formula (I)
In all cases, $Q^1$ and $Q^2$ represent oxygen
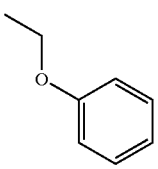
(I)
| Ex. No. | $R^1$ | $R^2$ | $R^3$ | $R^4$ | $R^5$ | $R^6$ | Physical Data |
|---|---|---|---|---|---|---|---|
| 43 | $CH_3$ | H | F | CN | 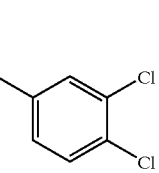 | $C_2H_5$ | m.p.: 222° C. logP = 2.96[a)] |
| 44 | $CH_3$ | H | F | CN | 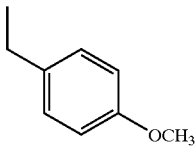 | $C_2H_5$ | m.p.: 142° C. logP = 2.52[a)] |
| 45 | $CH_3$ | H | F | CN | 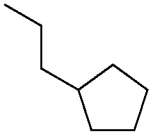 | $C_2H_5$ | m.p.: 221° C. logP = 2.58[a)] |
| 46 | $CH_3$ | H | F | CN | 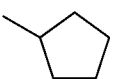 | $C_2H_5$ | m.p.: 143° C. logP = 3.34[a)] |
| 47 | $CH_3$ | H | F | CN | 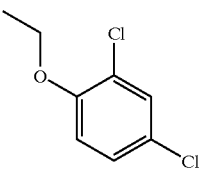 | $C_2H_5$ | m.p.: 93° C. logP = 2.66[a)] |
| 48 | $CH_3$ | H | F | CN | 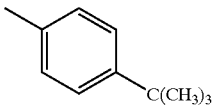 | $C_2H_5$ | m.p.: 175° C. logP = 3.35[a)] |
| 49 | $CH_3$ | H | F | CN |  | $C_2H_5$ | m.p.: 119° C. logP = 3.57[a)] |

TABLE 1-continued

Examples of the compounds of the formula (I)
In all cases, $Q^1$ and $Q^2$ represent oxygen (I)

| Ex. No. | $R^1$ | $R^2$ | $R^3$ | $R^4$ | $R^5$ | $R^6$ | Physical Data |
|---|---|---|---|---|---|---|---|
| 50 | $CH_3$ | H | F | CN | 3,5-dimethylphenyl | $C_2H_5$ | m.p.: 191° C. logP = 3.06[a) |
| 51 | $CH_3$ | H | F | CN | 4-ethoxyphenylethyl | $C_2H_5$ | m.p.: 74° C. logP = 3.22[a) |
| 52 | $CH_3$ | H | F | CN | 2,6-dichloro-4-methylpyridin-yl | $C_2H_5$ | m.p.: 227° C. |
| 53 | $CH_3$ | H | F | CN | 2,5-dichloro-4-methylthiazolyl | $C_2H_5$ | m.p.: 162° C. |
| 54 | $CH_3$ | H | F | CN | 6-chloro-3-methylpyridinyl | $C_2H_5$ | m.p.: 91° C. |
| 55 | $CH_3$ | H | F | CN | 3-methyl-2-(n-propylthio)pyridinyl | $C_2H_5$ | m.p.: 142° C. |
| 56 | $CH_3$ | H | F | CN | 2,3-dichloro-5-methylpyridinyl | $C_2H_5$ | m.p.: 83° C. |

TABLE 1-continued
Examples of the compounds of the formula (I)
In all cases, $Q^1$ and $Q^2$ represent oxygen
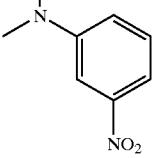
(I)
| Ex. No. | $R^1$ | $R^2$ | $R^3$ | $R^4$ | $R^5$ | $R^6$ | Physical Data |
|---|---|---|---|---|---|---|---|
| 57 | $CH_3$ | H | F | CN | 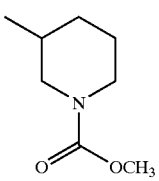 | $C_2H_5$ | m.p.: 255° C. |
| 58 | $CH_3$ | H | F | CN | 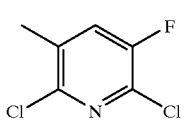 | $C_2H_5$ | m.p.: 104° C. |
| 59 | $CH_3$ | H | F | CN | 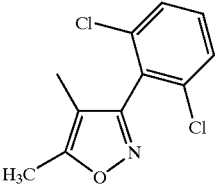 | $C_2H_5$ | m.p.: 218° C. |
| 60 | $CH_3$ | H | F | CN | 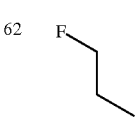 | $C_2H_5$ | m.p.: 223° C. |
| 61 | $CH_3$ | H | F | CN | $CHClCH_3$ | $C_2H_5$ | m.p.: 146° C. logP = 2.38[a)] |
| 62 | 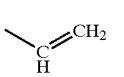 | H | F | CN | 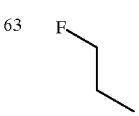 | $CH_3$ | m.p.: 142° C. logP = 1.93[a)] |
| 63 | 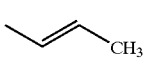 | H | F | CN | 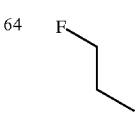 | $CH_3$ | m.p.: 85° C. logP = 2.12[a)] |
| 64 | 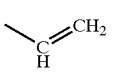 | H | F | CN | 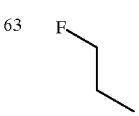 | $C_3H_7$-n | m.p.: 142° C. logP = 2.46[a)] |

TABLE 1-continued

Examples of the compounds of the formula (I)
In all cases, $Q^1$ and $Q^2$ represent oxygen

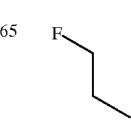

(I)

| Ex. No. | $R^1$ | $R^2$ | $R^3$ | $R^4$ | $R^5$ | $R^6$ | Physical Data |
|---|---|---|---|---|---|---|---|
| 65 |  | H | F | CN | $\!\!\!\!\diagdown\!\!\!\!\overset{\displaystyle CH_2}{\underset{H}{C}}$ | $C_2H_5$ | m.p.: 83° C. logP = 2.14[a)] |
| 66 | 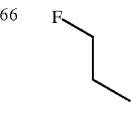 | H | F | CN | $\!\!\!\!\diagdown\!\!\!\!\overset{\displaystyle CH_2}{\underset{H}{C}}$ | $CH_3$ | m.p.: 96° C. logP = 2.35[a)] |
| 67 | $CH_3$ | H | F | CN |  | $C_2H_5$ | m.p.: 199° C. logP = 2.54[a)] |
| 68 | $CH_3$ | H | F | CN | 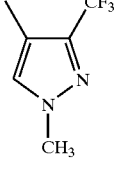 | $C_2H_5$ | m.p.: 189° C. logP = 1.73[a)] |
| 69 | $CH_3$ | H | F | CN | 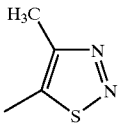 | $C_2H_5$ | m.p.: 192° C. logP = 2.05[a)] |
| 70 | $CH_3$ | H | F | CN |  | $C_2H_5$ | m.p.: 200° C. logP = 2.97[a)] |
| 71 | $CH_3$ | H | F | CN | 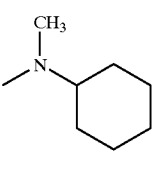 | $C_2H_5$ | m.p.: 188° C. logP = 2.92[a)] |
| 72 | $C_2H_5$ | H | F | CN | $\!\!\!\!\diagdown\!\!\!\!\overset{\displaystyle CH_2}{\underset{H}{C}}$ | $C_2H_5$ | m.p.: 143° C. logP = 2.27[a)] |

TABLE 1-continued

Examples of the compounds of the formula (I)

In all cases, $Q^1$ and $Q^2$ represent oxygen

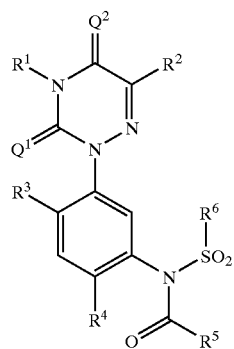

(I)

| Ex. No. | $R^1$ | $R^2$ | $R^3$ | $R^4$ | $R^5$ | $R^6$ | Physical Data |
|---|---|---|---|---|---|---|---|
| 73 | $CH_3$ | H | F | CN | 4-Cl-phenyl-OCH$_2$- | $C_2H_5$ | m.p.: 219° C. logP = 3.16[a)] |
| 74 | $CH_3$ | H | F | CN | 4-F-phenyl-OCH$_2$- | $C_2H_5$ | m.p.: 202° C. logP = 2.85[a)] |
| 75 | $CH_3$ | H | F | CN | (E)-4-CH$_3$-phenyl-CH=CH- | $C_2H_5$ | m.p.: 102° C. logP = 3.14[a)] |
| 76 | $CH_3$ | H | F | CN | 4-CH$_3$O-phenyl-(CH$_2$)$_3$- | $C_2H_5$ | logP = 3.03[a)] |
| 77 | $CH_3$ | H | F | CN | (E)-3,4-methylenedioxyphenyl-CH=CH- | $C_2H_5$ | m.p.: 141° C. logP = 2.72[a)] |

TABLE 1-continued

Examples of the compounds of the formula (I)
In all cases, $Q^1$ and $Q^2$ represent oxygen

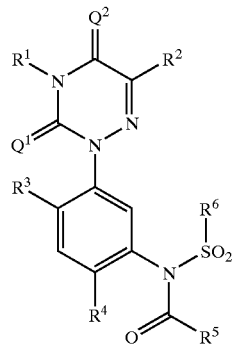

(I)

| Ex. No. | $R^1$ | $R^2$ | $R^3$ | $R^4$ | $R^5$ | $R^6$ | Physical Data |
|---|---|---|---|---|---|---|---|
| 78 | $CH_3$ | H | F | CN | 1,1-diphenylpropyl | $C_2H_5$ | m.p.: 183° C. logP = 3.48[a)] |
| 79 | $CH_3$ | H | F | CN | styryl | $C_2H_5$ | m.p.: 98° C. logP = 2.85[a)] |
| 80 | $CH_3$ | H | F | CN | 2-methoxyphenylethyl | $C_2H_5$ | m.p.: 140° C. logP = 2.70[a)] |
| 81 | $CH_3$ | H | F | CN | 2,5-dimethoxyphenylethyl | $C_2H_5$ | m.p.: 192° C. logP = 2.66[a)] |
| 82 | $CH_3$ | H | F | CN | 3-methoxyphenylethyl | $C_2H_5$ | m.p.: 158° C. logP = 2.63[a)] |

TABLE 1-continued

Examples of the compounds of the formula (I)
In all cases, $Q^1$ and $Q^2$ represent oxygen (I)

| Ex. No. | $R^1$ | $R^2$ | $R^3$ | $R^4$ | $R^5$ | $R^6$ | Physical Data |
|---|---|---|---|---|---|---|---|
| 83 | $CH_3$ | H | F | CN | 4-$CF_3$-C$_6$H$_4$ | $CH_3$ | |
| 84 | $CH_3$ | H | F | CN | 4-$CF_3$-C$_6$H$_4$ | $C_2H_5$ | |
| 85 | $C_2H_5$ | H | F | CN | 4-$CF_3$-C$_6$H$_4$ | $CH_3$ | |
| 86 | $C_2H_5$ | H | F | CN | 4-$CF_3$-C$_6$H$_4$ | $C_2H_5$ | |
| 87 | $CH_3$ | H | F | CN | 4-$OCF_3$-C$_6$H$_4$ | $CH_3$ | |
| 88 | $CH_3$ | H | F | CN | 4-$OCF_3$-C$_6$H$_4$ | $C_2H_5$ | |
| 89 | $C_2H_5$ | H | F | CN | 4-$OCF_3$-C$_6$H$_4$ | $CH_3$ | |

TABLE 1-continued

Examples of the compounds of the formula (I)
In all cases, $Q^1$ and $Q^2$ represent oxygen

| Ex. No. | $R^1$ | $R^2$ | $R^3$ | $R^4$ | $R^5$ | $R^6$ | Physical Data |
|---|---|---|---|---|---|---|---|
| 90 | $C_2H_5$ | H | F | CN | 4-(OCF$_3$)-C$_6$H$_4$ | $C_2H_5$ | |
| 91 | $CH_3$ | H | F | CN | 4-CN-C$_6$H$_4$ | $CH_3$ | |
| 92 | $CH_3$ | H | F | CN | 4-CN-C$_6$H$_4$ | $C_2H_5$ | |
| 93 | $C_2H_5$ | H | F | CN | 4-CN-C$_6$H$_4$ | $CH_3$ | |
| 94 | $C_2H_5$ | H | F | CN | 4-CN-C$_6$H$_4$ | $C_2H_5$ | |
| 95 | $CH_3$ | H | F | CN | 3-NO$_2$-C$_6$H$_4$ | $CH_3$ | |
| 96 | $CH_3$ | H | F | CN | 3-NO$_2$-C$_6$H$_4$ | $C_2H_5$ | |
| 97 | $C_2H_5$ | H | F | CN | 3-NO$_2$-C$_6$H$_4$ | $CH_3$ | |

TABLE 1-continued
Examples of the compounds of the formula (I)
In all cases, $Q^1$ and $Q^2$ represent oxygen
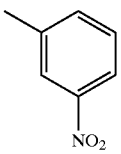
(I)
| Ex. No. | $R^1$ | $R^2$ | $R^3$ | $R^4$ | $R^5$ | $R^6$ | Physical Data |
|---|---|---|---|---|---|---|---|
| 98 | $C_2H_5$ | H | F | CN | 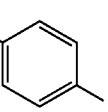 | $C_2H_5$ | |
| 99 | $CH_3$ | H | F | CN | 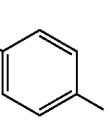 | $CH_3$ | |
| 100 | $CH_3$ | H | F | CN | 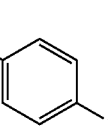 | $C_2H_5$ | |
| 101 | $C_2H_5$ | H | F | CN | 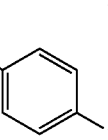 | $CH_3$ | |
| 102 | $C_2H_5$ | H | F | CN | 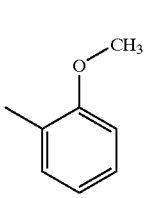 | $C_2H_5$ | |
| 103 | $CH_3$ | H | F | CN | 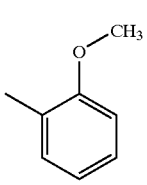 | $CH_3$ | |
| 104 | $CH_3$ | H | F | CN | 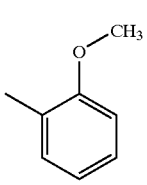 | $C_2H_5$ | |

TABLE 1-continued
Examples of the compounds of the formula (I)
In all cases, Q¹ and Q² represent oxygen
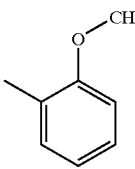
(I)
| Ex. No. | R¹ | R² | R³ | R⁴ | R⁵ | R⁶ | Physical Data |
|---|---|---|---|---|---|---|---|
| 105 | $C_2H_5$ | H | F | CN | 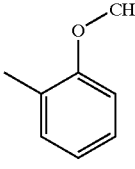 | $CH_3$ | |
| 106 | $C_2H_5$ | H | F | CN | 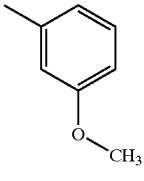 | $C_2H_5$ | |
| 107 | $CH_3$ | H | F | CN | 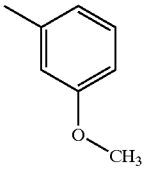 | $CH_3$ | |
| 108 | $CH_3$ | H | F | CN | 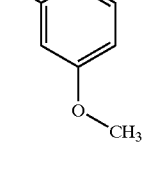 | $C_2H_5$ | |
| 109 | $C_2H_5$ | H | F | CN | 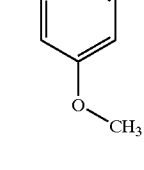 | $CH_3$ | |
| 110 | $C_2H_5$ | H | F | CN | 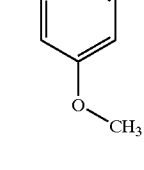 | $C_2H_5$ | |

TABLE 1-continued
Examples of the compounds of the formula (I)
In all cases, $Q^1$ and $Q^2$ represent oxygen
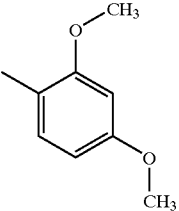
(I)
| Ex. No. | $R^1$ | $R^2$ | $R^3$ | $R^4$ | $R^5$ | $R^6$ | Physical Data |
|---|---|---|---|---|---|---|---|
| 111 | $CH_3$ | H | F | CN | 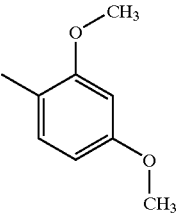 | $CH_3$ | |
| 112 | $CH_3$ | H | F | CN | 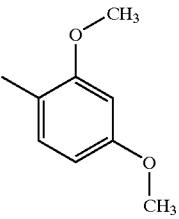 | $C_2H_5$ | |
| 113 | $C_2H_5$ | H | F | CN | 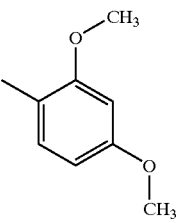 | $CH_3$ | |
| 114 | $C_2H_5$ | H | F | CN | 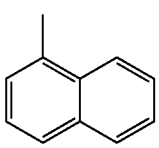 | $C_2H_5$ | |
| 115 | $CH_3$ | H | F | CN |  | $CH_3$ | |

TABLE 1-continued

Examples of the compounds of the formula (I)
In all cases, $Q^1$ and $Q^2$ represent oxygen

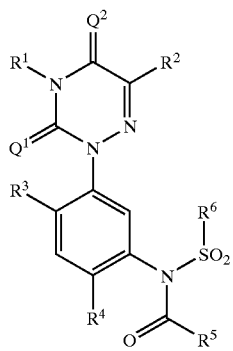

(I)

| Ex. No. | $R^1$ | $R^2$ | $R^3$ | $R^4$ | $R^5$ | $R^6$ | Physical Data |
|---|---|---|---|---|---|---|---|
| 116 | $CH_3$ | H | F | CN | 1-naphthyl | $C_2H_5$ | |
| 117 | $C_2H_5$ | H | F | CN | 1-naphthyl | $CH_3$ | |
| 118 | $C_2H_5$ | H | F | CN | 1-naphthyl | $C_2H_5$ | |

The logP values given in Table 1 were determined in accordance with EEC Directive 79/831 Annex V.A8 by HPLC (High Performance Liquid Chromatography) using a reversed-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—the corresponding measurement results are labelled in Table 1 with $^a$).

(b) Mobile phases for the determination in the neutral range: 0.01 molar aqueous phosphate buffer solution, acetonitrile; linear gradient from 10% acetonitrile to 90% acetonitrile—the corresponding measurement results are labelled in Table 1 with $^b$).

Calibration was carried out using unbranched alkan-2-ones (with from 3 to 16 carbon atoms) whose logP values are known (determination of the logP values by the retention times using linear interpolation between two successive alkanones).

The lambda max values were determined using the UV spectra from 200 nm to 400 nm in the maxima of the chromatographic signals.

Starting Materials of the Formula (II):
Example (II-1)

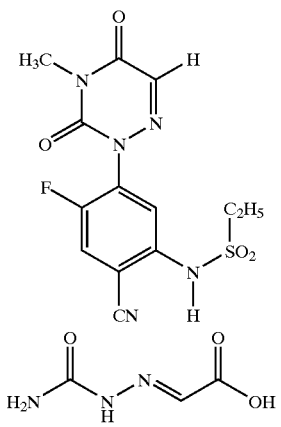

162.8 g (1.1 mol) of 50% strength aqueous glyoxalic acid are added rapidly to 111.5 g (1 mol) of semicarbazide hydrochloride in 1 liter of water. The mixture becomes slightly exothermic (about 27° C.), and the product precipitates out. For the reaction to go to completion, the mixture is initially stirred at room temperature for 30 minutes and then at 70° C. for 20 minutes. After cooling, the mixture is filtered off with suction and the product is washed with water and finally with acetone.

This gives 128.3 g (93% of theory) of glyoxalic acid semicarbazone of melting point 210° C. (decomp.).

Step 2

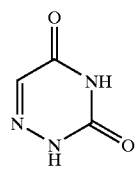

111.35 g (0.85 mol) of glyoxalic acid semicarbazone are initially charged in 1000 ml of 1,2-ethanediol and, a little at a time, 185 g (2.72 mol) of sodium ethoxide are introduced with cooling, at at most 40° C. After the exothermic reaction has ended, the mixture is heated to reflux temperature (about 110° C.) and stirred for 10 hours. The cooled clear solution is evaporated to dryness at 5 mbar (bath temperature 150° C.), the solid residue is admixed with about 1 liter of water, adjusted to pH 3–2 using conc. hydrochloric acid and, after cooling to 10° C., filtered off with suction, and the product is washed with water.

This gives 66.8 g (69% of theory) of 6-aza-uracil of melting point 279° C.

Step 3

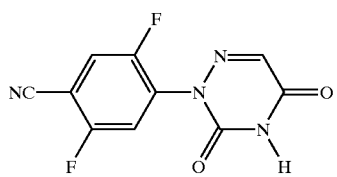

56.5 g (0.5 mol) of 6-aza-uracil in 600 ml of dimethyl sulphoxide are admixed with 69 g (0.5 mol) of potassium carbonate and 83.2 g (0.53 mol) of 2,4,5-trifluorobenzonitrile, and the mixture is stirred at from 70° C. to 80° C. for 10 hours. The mixture is then concentrated to about ⅓ of its original volume using a rotary evaporator, the residue is stirred with water and acidified with conc. hydrochloric acid and the precipitated product is filtered off with suction, washed with water and then with ethanol.

This gives 116 g (92.8% of theory) of 2-(2,5-difluoro-4-cyano-phenyl)-1,2,4-triazine-3,5(2H,4H)-dione of melting point >250° C.

logP (pH 2): 1.45

Step 4

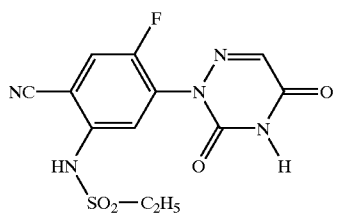

110 g (0.44 mol) of 2-(2,5-difluoro-4-cyano-phenyl)-1,2,4-triazine-3,5(2H,4H)-dione in 1200 ml of dimethyl sulphoxide are heated with 160 g (1.16 mol) of potassium carbonate and 58 g (0.52 mol) of ethanesulphonamide to from 125° C. to 130° C. and stirred at this temperature for 14 hours. The dark-green suspension is evaporated to dryness using a rotary evaporator, the residue is stirred with water and slowly (foaming, evolution of $CO_2$) adjusted to pH 3–4 using conc. hydrochloric acid, and precipitated product is filtered off with suction and washed with water.

This gives 117 g (78% of theory) of 2-(2-fluoro-4-cyano-5-ethylsulphonylamino-phenyl)-1,2,4-triazine-3,5(2H,4H)-dione of melting point 121 ° C. (decomp.).

logP (pH 2): 1.30

Step 5

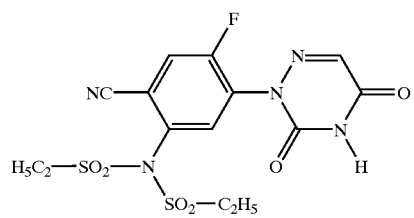

101.8 g (0.3 mol) of 2-(2-fluoro-4-cyano-5-ethylsulphonylamino-phenyl)-1,2,4-triazine-3,5(2H,4H)-dione and 47.0 g (0.34 mol) of potassium carbonate are initially charged in 1100 ml of acetonitrile, and 41.0 g (0.32 mol) of ethanesulphonyl chloride are added rapidly. The mixture is subsequently stirred at room temperature for 12 hours and concentrated under water-pump vacuum and the residue is stirred with water, adjusted to pH 2–3 using conc. hydrochloric acid, filtered off with suction, washed with water and isopropanol and dried.

This gives 106.2 g (76% of theory) of 2-(2-fluoro-4-cyano-5-ethylsulphonylamino-phenyl)-1,2,4-triazine-3,5 (2H,4H)-dione of melting point >250° C.

logP (pH 2): 2.07

Step 6

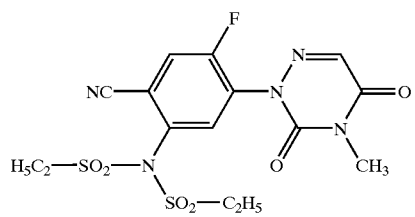

38.8 g (0.09 mol) of 2-(2-fluoro-4-cyano-5-ethylsulphonylamino-phenyl)-1,2,4-triazine-3,5(2H,4H)-dione and 13.8 g (0.1 mol) of potassium carbonate are stirred with 14.2 g (0.1 mol) of methyl iodide in 700 ml of acetonitrile at room temperature (about 20° C.) for 12 hours. The mixture is concentrated, the residue is stirred with water and acidified using conc. hydrochloric acid and the precipitated product is filtered off with suction and washed with water.

This gives 38 g (94% of theory) of 2-[2-fluoro-4-cyano-5-(bis-ethylsulphonyl)-amino-phenyl]-4-methyl-1,2,4-triazine-3,5(2H,4H)-dione of melting point 164° C.

logP (pH 2): 2.24

Step 7

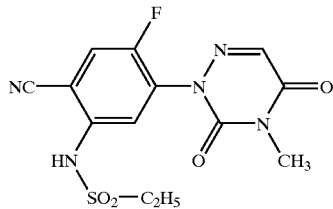

45.8 g (0.103 mol) of 2-[2-fluoro-4-cyano-5-(bis-ethylsulphonyl)-amino-phenyl]-4-methyl-1,2,4-triazine-3,5 (2H,4H)-dione and 18 g (0.22 mol) of sodium bicarbonate are stirred in 500 ml of acetone and 200 ml of water at reflux temperature for 12 hours, and the mixture is subsequently concentrated under water-pump vacuum. The residue is stirred in water and acidified with conc. hydrochloric acid, and precipitated product is filtered off with suction, washed with water, then stirred with ethanol, filtered off with suction, washed and dried.

This gives 32.3 g (89% of theory) of 2-(2-fluoro-4-cyano-5-ethylsulphonylamino-phenyl)-4-methyl-1,2,4-triazine-3,5 (2H,4H)-dione of melting point 233° C.

logP (pH 2): 1.66

USE EXAMPLES

Example A

Pre-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amount of active compound desired is applied per unit area. The concentration of the spray liquor is chosen so that the particular amount of active compound desired is applied in 1000 liter of water per hectare.

After three weeks, the degree of damage to the plants is rated in % damage in comparison to the development of the untreated control.

The figures denote:

0%=no effect (like untreated control)

100%=total destruction

In this test, for example, the compounds of Preparation Examples 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 35, 36, 37, 39, 40, 41, 42, 43, 44, 45, 46, 47, 48, 49, 50, 51 and 61 show very strong activity against weeds, whilst essentially being tolerated well by crop plants, such as, for example, barley, wheat, rapeseed, soya and sugar beet.

Example B

Post-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

In this test, for example, the compounds of Preparation Examples 2, 3, 4, 5, 6, 7, 8, 9, 10, 12, 13, 14, 16, 17, 18, 19, 20, 21, 22, 23, 24, 25, 26, 27, 28, 29, 30, 31, 32, 33, 35, 36, 37, 39, 40, 41, 42, 43, 44, 45, 46, 47, 48, 49, 50, 51 and 61 show very strong activity against weeds, whilst essentially being tolerated well by crop plants, such as, for example, barley and wheat.

What is claimed is:

1. A compound of the formula (I)

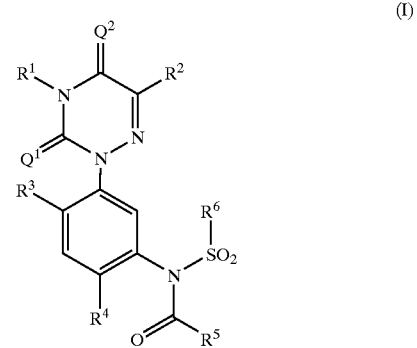

in which $Q^1$ represents oxygen or sulphur, $Q^2$ represents oxygen or sulphur, $R^1$ represents (i) hydrogen, cyano, or amino; (ii) an alkyl, alkoxy, alkylamino, dialkylamino, alkylcarbonyl, or alkoxycarbonyl group, each of which groups has 1 to 6 carbon atoms in the alkyl moiety and each of which groups is optionally cyano-, halogen- or $C_1$–$C_4$-alkoxy-substituted; (iii) an alkenyl, alkenylcarbonyl, alkenyloxycarbonyl, alkynyl, alkynylcarbonyl, or alkynyloxycarbonyl group, each of which groups has 2 to 6 carbon atoms in the alkenyl or alkynyl moiety and each of which groups is optionally halogen-substituted; or (iv) a cycloalkyl or cycloalkylalkyl group, each of which groups has 3 to 6 carbon atoms in the cycloalkyl moiety and optionally has 1 to 4 carbon atoms in the alkyl moiety and each of which groups is optionally cyano-, halogen-, or $C_1$–$C_4$-alkyl-substituted, $R^2$ represents (i) hydrogen, halogen, nitro, carboxyl, cyano, thiocarbamoyl, or amino; (ii) an alkyl, alkoxy, alkylthio, alkylamino, or dialkylamino group, each of which groups has 1 to 6 carbon atoms in the alkyl moiety and each of which groups is optionally cyano-, halogen-, or $C_1$–$C_4$-alkoxy-substituted; (iii) an alkenyl, alkenyloxy, alkenylthio, alkynyl, alkynyloxy, or alkynylthio group, each of which groups has 2 to 6 carbon atoms in the alkenyl or alkynyl moiety and each of which groups is optionally halogen-substituted; or (iv) a cycloalkyl or cycloalkylalkyl group, each of which groups has 3 to 6 carbon atoms in the cycloalkyl moiety and optionally has 1 to 6 carbon atoms in the alkyl moiety and each of which groups is optionally cyano-, halogen- or $C_1$–$C_4$-alkyl-substituted, $R^3$ represents hydrogen, cyano, or halogen, $R^4$ represents cyano or thiocarbamoyl, $R^5$ represents (i) hydrogen; (ii) alkoxycarbonyl having 1 to 6 carbon atoms in the alkoxy moiety; or (iii) one of the radicals —$R^7$, —O—$R^7$, —S$R^7$, —NH—$R^7$, or —N$R^7R^8$, $R^6$ represents (i) amino or hydroxyl or (ii) one of the radicals —$R^7$ or —N$R^7R^8$, $R^7$ represents (i) a straight-chain or branched alkyl that has 1 to 10 carbon atoms and is optionally mono- or polysubstituted by identical or different substituents selected from the group consisting of cyano; carboxyl; carbamoyl; thiocarbamoyl; halogen; an alkoxy, alkoxyalkoxy, alkylcarbonyloxy, alkylthio, alkylsulphinyl, alkylsulphonyl, alkoxycarbonyl, N-alkylaminocarbonyl, N,N-dialkyl-aminocarbonyl trialkylsilyl, or alkylsulphonylaminocarbonyl group, each of which groups is straight-chain or branched and has 1 to 6 carbon atoms in the individual alkyl moieties; or heterocyclyl, where the heterocyclyl radical is a furyl, furylmethyl, thienyl, oxazolyl, isoxazolyl, thiazolyl, pyrazolyl, oxadiazolyl, thiadiazolyl, pyridinyl, pyridinylmethyl, pyrimidinyl, pyrrolidinyl, piperidinyl, morpholinyl, or chromanyl group; (ii) an alkenyl or alkynyl group, each of which groups has 2 to 8 carbon atoms and is optionally mono- or polysubstituted by identical or different halogens; (iii) a cycloalkyl or cycloalkylalkyl group, each of which groups has 3 to 7 carbon atoms in the cycloalkyl moiety and optionally 1 to 4 carbon atoms in the alkyl moiety and each of which groups is optionally mono- or polysubstituted by identical or different substituents selected from the group consisting of cyano, halogen, and $C_1$–$C_4$-alkyl; or (iv) an aryl, bis-aryl-alkyl, arylalkenyl, arylalkyl, aryloxyalkyl, or arylalkoxyalkyl group, each of which groups has 6 to 10 carbon atoms in the aryl moiety and optionally up to 4 carbon atoms in the alkyl moiety or alkenyl moiety, each said moiety being straight-chain or branched, and each of which groups is optionally mono- or polysubstituted in the aryl moiety by identical or different substituents, or a heterocyclyl radical, where the heterocyclyl radical is a furyl, furylmethyl, thienyl, oxazolyl, isoxazolyl, thiazolyl, pyrazolyl, oxadiazolyl, thiadiazolyl, pyridinyl, pyridinylmethyl, pyrimidinyl, pyrrolidinyl, piperidinyl, morpholinyl, or chromanyl group that is optionally mono- or polysubstituted by identical or different substituents, wherein the aryl or heterocyclyl substituents are selected from the group consisting of halogen; cyano; nitro; amino; methylenedioxy; N—($C_1$–$C_4$-alkyl-carbonyl)amino; an alkyl, alkoxy, alkylthio, alkylsulphinyl, or alkylsulphonyl group, each of which groups is straight-chain or branched and has 1 to 6 carbon atoms; a halogenoalkyl, halogenoalkoxy, halogenoalkylthio, halogenoalkylsulphinyl, or halogenoalkylsulphonyl group, each of which groups is straight-chain or branched and has 1 to 6 carbon atoms and 1 to 3 identical or different halogen atoms; an alkoxycarbonyl or alkoximinoalkyl group, each of which groups is straight-chain or branched and has 1 to 6 carbon atoms in the individual alkyl moieties; and phenyl that is optionally mono- or polysubstituted by identical or different substituents selected from the group consisting of halogen, a straight-chain or branched alkyl or alkoxy group, each of which groups has 1 to 6 carbon atoms, and a straight-chain or branched halogenoalkyl or halogenoalkoxy group, each of which groups has 1 to 6 carbon atoms and 1 to 3 identical or different halogen atoms, and $R^8$ represents (i) hydrogen or represents straight-chain or branched alkyl that has 1 to 8 carbon atoms and is optionally mono- or polysubstituted by identical or different substituents selected from the group consisting of cyano; carboxyl; carbamoyl; thiocarbamoyl; halogen; an alkoxy, alkoxyalkoxy, alkylthio, alkylsulphinyl, alkylsulphonyl, alkoxycarbonyl, alkylaminocarbonyl, dialkylaminocarbonyl, trialkylsilyl, or alkylsulphonylaminocarbonyl group, each of which groups is straight-chain or branched and has 1 to 8 carbon atoms in the individual alkyl moieties; or heterocyclyl, where the heterocyclyl radical is a furyl, furylmethyl, thienyl, oxazolyl, isoxazolyl, thiazolyl, pyrazolyl, oxadiazolyl, thiadiazolyl, pyridinyl, pyridinylmethyl, pyrimidinyl, pyrrolidinyl, piperidinyl, morpholinyl, or chromanyl group; (ii) an alkenyl or alkynyl group, each of which groups has 2 to 8 carbon atoms and each of which groups is optionally mono- or polysubstituted by identical or different halogens; or (iii) cycloalkyl having 3 to 7 carbon atoms that is optionally mono- or polysubstituted by identical or different substituents selected from the group consisting of cyano, halogen, and straight-chain or branched alkyl having 1 to 4 carbon atoms, or $R^8$ together with $R^7$ represents alkanediyl that has 2 to 6 carbon atoms and is optionally interrupted by O, S, NH, or N—($C_1$–$C_4$-alkyl).

2. A compound according to claim 1 wherein $R^1$ represents (i) hydrogen, cyano, or amino; (ii) a methyl, ethyl, n- or i-propyl, n-, i-, s-, or t-butyl, methoxy, ethoxy, n- or i-propoxy, n-, i-, s-, or t-butoxy, methylamino, ethylamino, n- or i-propylamino, n-, i-, s-, or t-butylamino, dimethylamino, diethylamino, acetyl, propionyl, n- or i-butyroyl, methoxycarbonyl, ethoxycarbonyl, or n- or i-propoxycarbonyl group, each of which groups is optionally cyano-, fluorine-, chlorine-, methoxy-, or ethoxy-substituted; (iii) a propenyl, butenyl, propenylcarbonyl, butenylcarbonyl, propenyloxycarbonyl, or butenyloxycarbonyl group, each of which groups is optionally fluorine-, chlorine-, or bromine-substituted; (iv) propynyl, butynyl, propynylcarbonyl, butynylcarbonyl, propynyloxycarbonyl, or butynyloxycarbonyl; or (v) a cyclopropyl, cyclobutyl, cyclopentyl, cyclohexyl, cyclopropylmethyl, cyclobutylmethyl, cyclopentylmethyl, or cyclohexylmethyl group, each of which groups is optionally cyano-, fluorine-, chlorine-, bromine-, methyl-, or ethyl-substituted, $R^2$ represents (i) hydrogen, nitro, carboxyl, cyano, thiocarbamoyl, amino, fluorine, chlorine, or bromine; (ii) a methyl, ethyl, n- or i-propyl, n-, i- s-, or t-butyl, methoxy, ethoxy, n- or i-propoxy, n-, i-, s-, or t-butoxy, methylthio, ethylthio, n- or i-propylthio, n-, i-, s-, or t-butylthio, methylamino, ethylamino, n- or i-propylamino, n-, i-, s-, or t-butylamino, dimethylamino, or diethylamino group, each of which groups is optionally cyano-, fluorine-, chlorine-, methoxy-, or ethoxy-substituted; (iii) a propenyl, propenyloxy, propenylthio, butenyl, butenyloxy, or butenylthio group, each of which groups is optionally fluorine-, chlorine-, or bromine-substituted; (iv) propynyl, propynyloxy, propynylthio, butynyl, butynyloxy, or butynylthio; or (v) a cyclopropyl, cyclobutyl, cyclopentyl, cyclohexyl, cyclopropylmethyl, cyclobutylmethyl, cyclopentylmethyl, or cyclohexylmethyl group, each of which groups is optionally cyano-, fluorine-, chlorine-, bromine-, methyl-, or ethyl-substituted, $R^3$ represents hydrogen, fluorine, or chlorine, $R^5$ represents (i) hydrogen, methoxycarbonyl, ethoxycarbonyl, or n- or i-propoxycarbonyl, or (ii) one of the radicals —$R^7$, —O—$R^7$, —S—$R^7$, —NH—$R^7$, or —$NR^7R^8$, $R^7$ represents (i) a methyl, ethyl, n- or i-propyl, n-, i-, s-, or t-butyl, n-, i-, s-, t-, or neo-pentyl, n-, i-, or s-hexyl group, each of which groups is optionally mono- or disubstituted by a substituent selected from the group consisting of cyano, carboxyl, carbamoyl, fluorine, chlorine, bromine, methoxy, ethoxy, n- or i-propoxy, methoxymethoxy, ethoxymethoxy, methoxyethoxy, ethoxyethoxy, acetylmethoxy, methylthio, ethylthio, n- or i-propylthio, methylsulphinyl, ethylsulphinyl, methylsulphonyl, ethylsulphonyl, methoxycarbonyl, ethoxycarbonyl, methylaminocarbonyl, ethylaminocarbonyl, dimethylaminocarbonyl trimethylsilyl, methylsulphonylaminocarbonyl, and ethylsulphonylaminocarbonyl; (ii) an ethenyl, propenyl, butenyl, ethynyl, propynyl, or butynyl group, each of which groups is optionally mono- or disubstituted by fluorine and/or chlorine; (iii) a cyclopropyl, cyclobutyl, cyclopentyl, cyclohexyl, cyclopropylmethyl, cyclopropylethyl, cyclopentylmethyl, cyclopentylethyl, cyclohexylmethyl, or cyclohexylethyl group, each of which groups is optionally mono- or disubstituted by identical or different substituents selected from the group consisting of fluorine, chlorine, methyl, and ethyl; or (iv) a phenyl, benzyl, phenylethyl, phenylpropyl, phenoxymethyl, 2,2-bis-phenyl-ethyl, phenylethenyl, phenoxyethyl, phenoxypropyl, furyl, furylmethyl, thienyl, oxazolyl, isoxazolyl, thiazolyl, pyrazolyl, oxadiazolyl, thiadiazolyl, pyridinyl, pyridinylmethyl, pyrimidinyl, pyrrolidinyl, piperidinyl, morpholinyl, or chromanyl group, each of which groups is optionally mono-, di-, or trisubstituted by identical or different substituents selected from the group consisting of fluorine, chlorine, bromine, cyano, nitro, amino, methylenedioxy, N-acetylamino, methyl, ethyl, n- or i-propyl, n-, i-, s-, or t-butyl, methoxy, ethoxy, n- or i-propoxy, n-, i-, s-, or t-butoxy, methylthio, ethylthio, methylsulphinyl, methylsulphonyl, trifluoromethyl, difluoromethyl, trifluoromethoxy, difluoromethoxy, trifluoromethylthio, trifluoromethylsulphinyl, trifluoromethylsulphonyl, methoxycarbonyl, ethoxycarbonyl, methoximinomethyl, methoximinoethyl, ethoximinomethyl, and ethoximinoethyl, and $R^8$ represents (i) hydrogen or represents a methyl, ethyl, n- or i-propyl, or n- or i-butyl group, each of which groups is optionally substituted with a substituent selected from the group consisting of cyano, carboxyl, carbamoyl, fluorine, chlorine, methoxy, ethoxy, n- or i-propoxy, methoxymethoxy, ethoxymethoxy, methoxyethoxy, ethoxyethoxy, methylthio, ethylthio, n- or i-propylthio, methylsulphinyl, ethylsulphinyl, methylsulphonyl, ethylsulphonyl, methoxycarbonyl, ethoxycarbonyl, methylaminocarbonyl, ethylaminocarbonyl, and dimethylaminocarbonyl; (ii) an ethenyl, propenyl, butenyl, ethynyl, propynyl, or butynyl group, each of which groups is optionally mono- or disubstituted by fluorine and/or chlorine; or (iii) a cyclopropyl, cyclopentyl, or cyclohexyl group, each of which groups is optionally mono- or disubstituted by identical or different substituents selected from the group consisting of fluorine, chlorine, methyl, and ethyl, or $R^8$ together with $R^7$ represents butane-1,4-diyl, pentane-1,5-diyl, or 3-oxa-pentane-1,5-diyl.

3. A compound according to claim 1 wherein $R^1$ represents (i) hydrogen or (ii) a methyl, ethyl, n- or i-propyl group, each of which groups is optionally fluorine-substituted, $R^2$ represents (i) hydrogen, cyano, fluorine, chlorine, or bromine or (ii) a methyl, ethyl, or n- or i-propyl group, each of which groups is optionally fluorine-substituted, $R^5$ represents (i) hydrogen or (ii) one of the radicals —$R^7$, —O—$R^7$, —S—$R^7$, —NH—$R^7$, or —$NR^7R^8$, $R^7$ represents (i) a methyl, ethyl, n- or i-propyl, n-, i-, s-, or t-butyl, n-, i-, s-, t-, or neo-pentyl group, each of which groups is optionally mono- or disubstituted by substituents selected from the group consisting of cyano, fluorine, chlorine, bromine, methoxy, ethoxy, n- or i-propoxy, methoxymethoxy, ethoxymethoxy, methoxyethoxy, ethoxyethoxy, and acetylmethoxy; (ii) an ethenyl, propenyl, butenyl, ethynyl, propynyl, or butynyl group, each of which groups is optionally mono- or disubstituted by fluorine and/or chlorine; (iii) a cyclopropyl, cyclobutyl, cyclopentyl, cyclohexyl, cyclopropylmethyl, cyclopropylethyl, cyclopentylmethyl, cyclopentylethyl, cyclohexylmethyl, or cyclohexylethyl group, each of which groups is optionally mono- or disubstituted by identical or different substituents selected from the group consisting of fluorine, chlorine, methyl, and ethyl; or (iv) a phenyl, benzyl, phenylethyl, phenylpropyl, 2,2-bis-phenyl-ethyl, phenylethenyl, phenoxymethyl, phenoxyethyl, phenoxypropyl, furyl, thienyl, oxazolyl, isoxazolyl, thiazolyl, pyrazolyl, oxadiazolyl, thiadiazolyl, pyridinyl, pyrimidinyl, pyrrolidinyl, piperidinyl, or chromanyl group, each of which groups is optionally mono-, di-, or trisubstituted by identical or different substituents selected from the group consisting of fluorine, chlorine, bromine, cyano, nitro, methylenedioxy, methyl, ethyl, n- or i-propyl, n-, i-, s-, or t-butyl, methoxy, ethoxy, n- or i-propoxy, methylthio, ethylthio, methylsulphinyl, methylsulphonyl, trifluoromethyl, difluoromethyl, trifluoromethoxy, and difluoromethoxy, and $R^8$ represents (i) hydrogen or represents a methyl, ethyl, n- or i-propyl, or n- or i-butyl group, each of which groups is optionally monosubstituted by substituents selected from the group consisting of cyano, fluorine, chlorine, methoxy, ethoxy, and n- or i-propoxy; (ii) an ethenyl, propenyl, butenyl, ethynyl, propynyl, or buty nyl group, each of which groups is optionally mono- or disubstituted by fluorine and/or chlorine; or (iii) a cyclopropyl, cyclopentyl, or cyclohexyl group, each of which groups is optionally mono- or disubstituted by identical or different substituents selected from the group consisting of fluorine, chlorine, methyl, and ethyl.

4. A compound having the formula

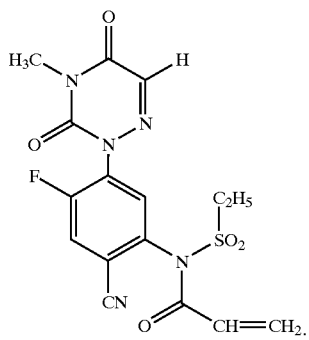

5. A compound having the formula

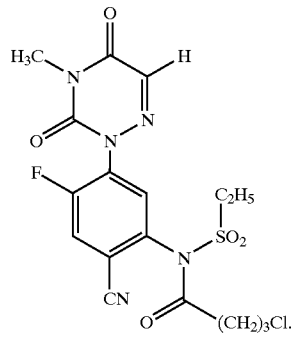

6. A compound having the formula

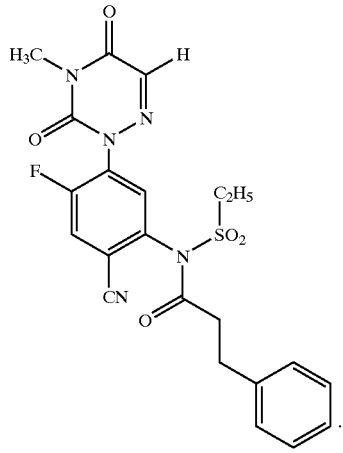

7. A compound having the formula

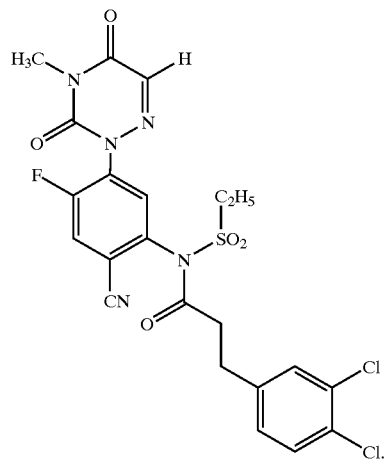

8. A compound having the formula

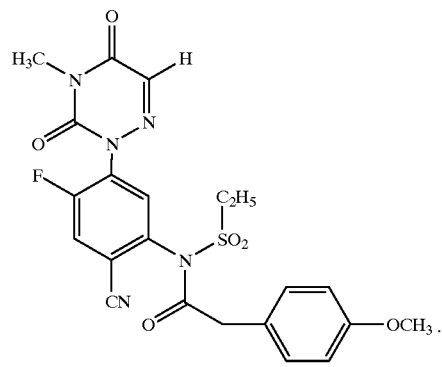

9. A compound having the formula

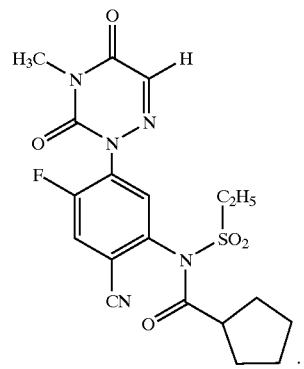

10. A compound having the formula

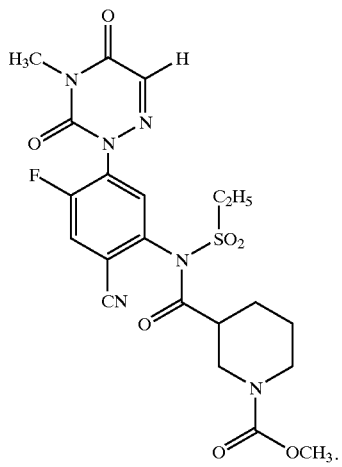

11. A compound having the formula

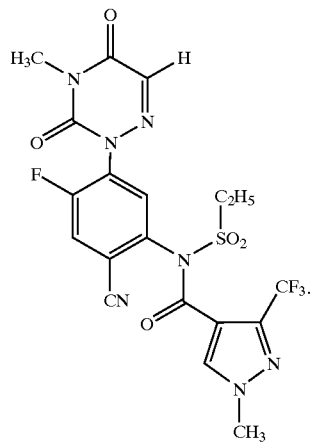

12. A process for preparing a compound according to claim 1 comprising reacting a 2-aryl-1,2,4-triazine-3,5-di(thi)one of the formula (II)

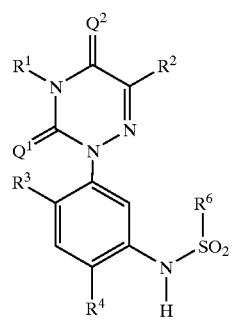

in which $Q^1$, $Q^2$, $R^1$, $R^2$, $R^3$, $R^4$, and $R^6$ are each as defined in claim 1, with a halogenocarbonyl compound of the formula (III)

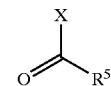

in which
$R^5$ is as defined in claim 1, and
X represents halogen,
optionally in the presence of a reaction auxiliary and optionally in the presence of a diluent.

13. A method for controlling undesirable vegetation comprising allowing an herbicidally effective amount of one or more compounds according to claim 1 to act on undesirable plants and/or their habitat.

14. A method for controlling undesirable vegetation comprising allowing an herbicidally effective amount of one or more compounds according to claim 4 to act on undesirable plants and/or their habitat.

15. A method for controlling undesirable vegetation comprising allowing an herbicidally effective amount of one or more compounds according to claim 5 to act on undesirable plants and/or their habitat.

16. A method for controlling undesirable vegetation comprising allowing an herbicidally effective amount of one or more compounds according to claim 6 to act on undesirable plants and/or their habitat.

17. A method for controlling undesirable vegetation comprising allowing an herbicidally effective amount of one or more compounds according to claim 7 to act on undesirable plants and/or their habitat.

18. A method for controlling undesirable vegetation comprising allowing an herbicidally effective amount of one or more compounds according to claim 8 to act on undesirable plants and/or their habitat.

19. A method for controlling undesirable vegetation comprising allowing an herbicidally effective amount of one or more compounds according to claim 9 to act on undesirable plants and/or their habitat.

20. A method for controlling undesirable vegetation comprising allowing an herbicidally effective amount of one or more compounds according to claim 10 to act on desirable plants and/or their habitat.

21. A method for controlling undesirable vegetation comprising allowing an herbicidally effective amount of one or more compounds according to claim 11 to act on undesirable plants and/or their habitat.

22. An herbicidal composition comprising a compound according to claim 1 and customary extenders and/or surfactants.

23. An herbicidal composition comprising a compound according to claim 4 and customary extenders and/or surfactants.

24. An herbicidal composition comprising a compound according to claim 5 and customary extenders and/or surfactants.

25. An herbicidal composition comprising a compound according to claim 6 and customary extenders and/or surfactants.

26. An herbicidal composition comprising a compound according to claim 7 and customary extenders and/or surfactants.

27. An herbicidal composition comprising a compound according to claim 8 and customary extenders and/or surfactants.

28. An herbicidal composition comprising a compound according to claim 9 and customary extenders and/or surfactants.

29. An herbicidal composition comprising a compound according to claim 10 and customary extenders and/or surfactants.

30. An herbicidal composition comprising a compound according to claim 11 and customary extenders and/or surfactants.

* * * * *

UNITED STATES PATENT AND TRADEMARK OFFICE
CERTIFICATE OF CORRECTION

PATENT NO.    : 6,608,004 B2
DATED         : August 19, 2003
INVENTOR(S)   : Karl-Heinz Linker et al.

It is certified that error appears in the above-identified patent and that said Letters Patent is hereby corrected as shown below:

Title page,
Item [22] PCT Filed, should read -- [22] PCT Filed: May 24, 2000 --.

Column 1,
Line 4, delete "This is a 371 of PCT/EP00/04704, filed May 24, 2001" and insert -- This is a 371 of PCT/EP00/04704, filed May 24, 2000. --

Signed and Sealed this

Ninth Day of August, 2005

JON W. DUDAS
*Director of the United States Patent and Trademark Office*